United States Patent [19]

Shuto et al.

[11] Patent Number: 5,258,410

[45] Date of Patent: Nov. 2, 1993

[54] AROMATIC COMPOUNDS, THEIR PRODUCTION PROCESSES AND THEIR COMPOSITIONS FOR THE CONTROL OF INSECT PESTS

[75] Inventors: Akira Shuto; Noriyasu Sakamoto; Hirosi Kisida, all of Hyogo; Hiroaki Fujimoto; Kimitoshi Umeda, both of Osaka, all of Japan

[73] Assignee: Sumitomo Chemical Company Limited, Osaka, Japan

[21] Appl. No.: 775,106

[22] Filed: Oct. 11, 1991

[30] Foreign Application Priority Data

Oct. 11, 1990 [JP] Japan ................................. 2-274985
May 15, 1991 [JP] Japan ................................. 3-140998

[51] Int. Cl.$^5$ ..................... A01K 87/075; C07C 43/11
[52] U.S. Cl. ..................... 514/721; 568/637; 568/640
[58] Field of Search ................ 568/637, 640; 514/721

[56] References Cited

U.S. PATENT DOCUMENTS

| | | |
|---|---|---|
| 2,213,214 | 9/1940 | Hester . |
| 2,817,622 | 12/1957 | Obladen . |
| 3,987,102 | 10/1976 | Karrer . |
| 3,987,108 | 10/1976 | Karrer . |
| 4,088,776 | 5/1978 | Karrer . |
| 4,094,989 | 6/1978 | Karrer . |
| 4,153,731 | 5/1979 | Karrer . |

*Primary Examiner*—Marianne M. Cintins
*Assistant Examiner*—Rebecca Cook
*Attorney, Agent, or Firm*—Birch, Stewart, Kolasch & Birch

[57] ABSTRACT

An aromatic compound of the formula

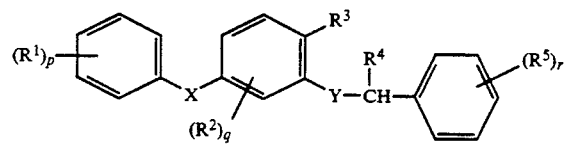

, which is useful as an insect pest controlling agent.

19 Claims, No Drawings

AROMATIC COMPOUNDS, THEIR PRODUCTION PROCESSES AND THEIR COMPOSITIONS FOR THE CONTROL OF INSECT PESTS

BACKGROUND OF THE INVENTION

1. Field of the Invention

The present invention relates to aromatic compounds, their production processes and their compositions for the control of insect pests.

2. Description of the Prior Art

It is described in U.S. Pat. Nos. 3,987,102, 4,094,989 and 4,153,731 that certain aromatic compounds are useful as insecticides and acaricides. But, their insecticidal and acaricidal activities are still not satisfactory.

SUMMARY OF THE INVENTION

As a result of the extensive study seeking aromatic compounds producing a satisfactory controlling effect on insect pests, it has been found that those of the following formula exhibit a remarkable juvenile hormone-like activity and can control significantly the growth of insect pests:

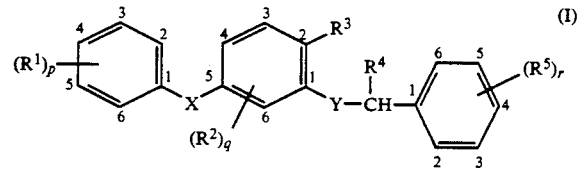

wherein $R^1$ is, the same or different, a hydrogen atom, a halogen atom, a $C_1$-$C_4$ alkyl group, a $C_1$-$C_4$ haloalkyl group, a $C_1$-$C_3$ alkoxy group, a $C_1$-$C_3$ haloalkoxy group, a cyano group or a nitro group, or two adjacent $R^1$s may be combined together to represent a methylenedioxy group optionally bearing one or two substituents selected from halogen and methyl; $R^2$ is, the same or different, a hydrogen atom, a halogen atom or a methyl group; $R^3$ is a halogen atom or a $C_1$-$C_3$ alkyl group; $R^4$ is a hydrogen atom or a $C_1$-$C_3$ alkyl group; $R^5$ is, the same or different, a halogen atom, a $C_1$-$C^3$ alkyl group, a $C_1$-$C^3$ haloalkyl group, a $C_1$-$C^3$ alkoxy group or a $C_1$-$C^3$ haloalkoxy group, or two adjacent $R^5$s may be combined together to represent a methylenedioxy group optionally bearing one or two substituents selected from halogen and methyl; X is an oxygen atom (—O—), a sulfur atom (—S—), a carbonyl group (—CO—), a sulfinyl group (—SO—), a sulfonyl group (—SO$_2$—), an imino group (—NH—) or a methylene group (—CH$_2$—); Y is an oxygen atom (—O—) or a sulfur atom (—S—); p is an integer of 1 to 5; q is an integer of 1 to 3; and r is an integer of 1 to 5. The present invention is based on the above finding.

DETAILED DESCRIPTION OF THE INVENTION

The aromatic compounds (I) of the invention have an excellent juvenile hormone-like activity against insect pests. They exhibit various actions such as metamorphosis inhibition, embryogenesis inhibition and sterilization and are thus efficacious as growth regulators, chemosterilants, ovicides or reproduction inhibitory agents on various insect pests such as agricultural, forestal, hygienic and stored grain insect pests. They are also efficacious against insect pests having an increased resistance to commercial insecticides.

In the formula (I) which represents the aromatic compounds of the invention, examples of the halogen atom are fluorine, chlorine, bromine, iodine, etc. Examples of the $C_1$-$C_3$ alkyl group are methyl, ethyl, n-propyl, isopropyl, etc., while examples of the $C_1$-$C_4$ alkyl group are methyl, ethyl, n-propyl, isopropyl, n-butyl, sec-butyl, isobutyl, tert-butyl, etc. Examples of the $C_1$-$C_3$ haloalkyl group include trifluoromethyl, difluoromethyl, 2-fluoroethyl, 1-fluoroethyl, 1,2-difluoroethyl, 2,2,2-trifluoroethyl, 2-chloroethyl, 3-fluoro-n-propyl, 2-fluoro-n-propyl, 1-fluoro-n-propyl, 3-chloro-n-propyl, 3-bromo-n-propyl, etc., while examples of the $C_1$-$C_4$ haloalkyl group include trifluoromethyl, difluoromethyl, 2-fluoroethyl, 1-fluoroethyl, 1,2-difluoroethyl, 2,2,2-trifluoroethyl, 2-chloroethyl, 3-fluoro-n-propyl, 2-fluoro-n-propyl, 1-fluoro-n-propyl, 3-chloro-n-propyl, 3-bromo-n-propyl, 4-fluoro-n-butyl, 4-chloro-n-butyl, etc. Examples of the $C_1$-$C_3$ alkoxy group cover methoxy, ethoxy, n-propoxy, isopropoxy, etc. Examples of the $C_1$-$C_3$ haloalkoxy group cover trifluoromethoxy, difluoromethoxy, bromodifluoromethoxy, chlorodifluoromethoxy, 2-fluoroethoxy, 2,2,2-trifluoroethoxy, perfluoroethoxy, 1,1,2-trifluoroethoxy, 1-fluoroethoxy, 1,2-difluoroethoxy, 2-chloro-1,1,2-trifluoroethoxy, 3-fluoro-n-propoxy, 1-fluoro-n-propoxy, 2-fluoro-n-propoxy, perfluoro-n-propoxy, 2-chloroethoxy, 3-chloro-n-propoxy, 3-bromo-n-propoxy, 1,1,2,2-tetrafluoroethoxy, 1,1-difluoromethoxy, etc.

Among the aromatic compounds (I), preferred are those wherein $R^1$ is, the same or different, a hydrogen atom, a fluorine atom, a chlorine atom, a bromine atom, a methyl group or a trifluoromethyl group, $R^2$ is a hydrogen atom or a chlorine atom, $R^3$ is a fluorine atom, a chlorine atom, a bromine atom or a methyl group, $R^4$ is a hydrogen atom or a methyl group, $R^5$ is, the same or different, a chlorine atom, a methyl group or an ethyl group, X is an oxygen atom or a methylene group, Y is an oxygen atom, p and r are each an integer of 1 or 2 and q is an integer of 1. More preferred are those wherein $R^1$ is, the same or different, a hydrogen atom, a fluorine atom or a chlorine atom, $R^2$ is a hydrogen atom, $R^3$ is a chlorine atom, $R^4$ is a hydrogen atom, $R^5$ is a chlorine atom or a methyl group, X is an oxygen atom or a methylene group, Y is an oxygen atom, p is an integer of 1 or 2 and q and r are each an integer of 1. Most preferred are those wherein $(R^1)_p$ is 3,5-$F_2$ or 3-Cl, $R^2$ is a hydrogen atom, $R^3$ is a chlorine atom, $R^4$ is a hydrogen atom, $R^5$ is a chlorine atom or a methyl group, X is an oxygen atom, Y is an oxygen atom and q and r are each an integer of 1.

Further, $R^5$ may be present at any position from the 2 to 6-positions on the benzene ring but is preferred to exist at least at the 4-position.

The aromatic compounds (I) of the invention can be produced by various processes, among which typical examples are shown below.

Process A

The aromatic compound (I) is produced by reacting a (thio)phenol compound of the formula:

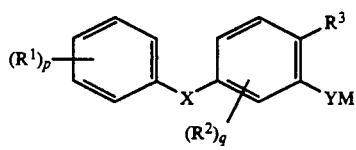

wherein M is an alkali metal atom or a hydrogen atom and $R^1$, $R^2$, $R^3$, X, Y, p and q are each as defined above with a halide of the formula:

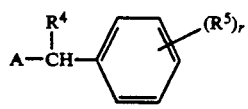

wherein A is a halogen atom and $R^4$, $R^5$ and r are each as defined above.

The reaction may be carried out usually in an inert solvent in the presence of a base at a temperature of from about $-20°$ C. to the boiling point of the inert solvent, preferably from about $-5°$ C. to the boiling point of the inert solvent. When the (thio)phenol compound (II) is employed in a metal salt form, the base is not necessarily required to use.

The molar proportion of the (thio)phenol compound (II) and the halide (III) to be used for the reaction is not limitative but is preferred to be nearly equal. Examples of the inert solvent are lower alcohols (e.g. methanol, ethanol, propanol, isopropanol, tert-butanol), ketones (e.g. acetone, methyl ethyl ketone), hydrocarbons (e.g. hexane, benzene, toluene), ethers (e.g. diethyl ether, diisbpropyl ether, tetrahydrofuran, dioxane), acid amides (e.g. N,N-dimethylformamide, hexamethylphosphoric triamide), halogenated hydrocarbons (e.g. dichloromethane, chloroform, 1,2-dichloroethane, chlorobenzene), nitriles (e.g. acetonitrile), nitro compounds (e.g. nitromethane), dimethyl sulfoxide, sulforane, water and mixtures thereof. Example of the base are alkali metal hydroxides (e.g. sodium hydroxide, potassium hydroxide), alkali metal carbonates (e.g. sodium carbonate, potassium carbonate), alkali metals (e.g. metallic sodium), alkali metal hydrides (e.g. sodium hydride), organic bases (e.g. sodium methoxide, sodium ethoxide, triethylamine, pyridine), etc. When necessary or desired, an ammonium salt such as triethylbenzylammonium chloride or tetrabutylammonium bromide may be added to the reaction system as a catalyst.

After completion of the reaction, post-treatment may follow in a per se conventional manner such as extraction with an organic solvent and concentration. When necessary or desired, the product may further be purified by chormatography, distillation, recrystatllization, etc.

Process B

The aromatic compound (I) wherein Y is an oxygen atom is produced by reacting a phenol compound of the formula:

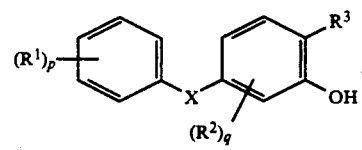

wherein $R^1$, $R^2$, $R^3$, X, p and q are each as defined above with an alcohol of the formula:

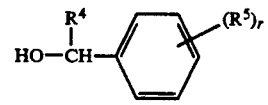

wherein $R^4$, $R^5$ and r are each as defined above. This process is advantageously applicable when $R^4$ is other than a hydrogen atom.

The reaction may be carried out normally in an inert solvent in the presence of a dehydrating catalyst or agent at a temperature of from about $-20°$ to $200°$ C. or the boiling point of the inert solvent.

The molar proportion of the phenol compound (IV) and the alcohol (V) is not limitative but is preferred to be nearly equal. Examples of the dehydrating catalyst are inorganic acids (e.g. hydrochloric acid, sulfuric acid), aromatic sulfonic acids, sulfonic acid halides, etc. Examples of the dehydrating agent include dicyclohexylcarbodimide, diisopropyl azodicarboxylate with triphenylphosphine, diethyl azodicarboxylate with triphenylphosphine, etc. Examples of the inert solvent are hydrocarbons (e.g. benzene, toluene, xylene), ethers (e.g. diethyl ether, diisopropyl ether, tetrahydrofuran, dioxane), halogenated hydrocarbons (e.g. carbon tetrachloride, dichloromethane, 1,2-dichloroethane, chlorobenzene, dichlorobenzene), etc.

After completion of the reaction, post-treatment may follow in a per se conventional manner such as extraction with an organic solvent and concentration. When necessary or desired, the product may further be purified by chromatography, distillation, recrystallization, etc.

The aromatic compounds (I) of the invention have some asymmetric carbon atoms and can form optical isomers. Those optical isomers and their mixtures fall within the scope of the invention.

Among the starting compounds in the above processes, the (thio)phenol compound (II) wherein Y is an oxygen atom and M is an alkali metal atom can be prepared from the corresponding phenol compound (IV) (i.e. the compound of the formula (II) wherein Y is an oxygen atom and M is a hydrogen atom).

The (thio)phenol compound (II) wherein Y is an sulfur atom and M is an alkali metal atom can be prepared from the corresponding thiophenol compound of the formula:

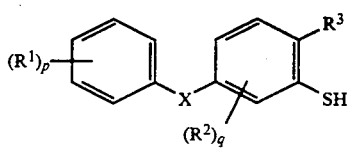

wherein $R^1$, $R^2$, $R^3$, X, p and q are each as defined above (i.e. the compound of the formula (II) wherein Y is a sulfur atom and M is a hydrogen atom).

The phenol compound (IV) can be synthesized from any appropriate commercial product by a conventional procedure. For instance, the phenol compound (IV) wherein $R^3$ is a chlorine atom may be prepared by reacting the corresponding non-chlorinated compound, i.e. a phenol compound, of the formula:

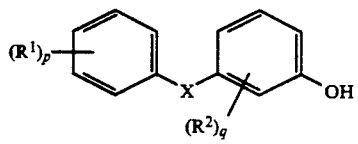

(VII)

wherein $R^1$, $R^2$, X, p and q are each as defined above (i.e. the compound of the formula (IV) wherein $R^3$ is a hydrogen atom) with a chlorinating agent, preferably in an inert solvent according to the method as described in J.Am.Chem.Soc., 73, 2723 (1951), J.Org.Chem., 39, 1160 (1974), etc. The molar proportion of the phenol compound (VII) and the chlorinating agent is not limitative but it is ordinary to use the chlorinating agent in an amount equivalent to the phenol compound (VII) or somewhat in excess. Examples of the chlorinating agent are chlorine, tert-butyl hypochlorite, sulfuryl chloride, etc. If necessary and desired, the reaction can be carried out in the presence of an inert solvent. Examples of the solvent are dichloromethane, 1,2-dichloroethane, carbon tetrachloride, benzene, acetic acid, etc. The chlorinating agent itself may be available as a reaction medium when it is in liquid. The reaction temperature is usually from about −80° C. to the refluxing temperature of the reaction system, preferably from about −20° C. to the refluxing temperature of the reaction system.

After completion of the reaction, post-treatment may follow in a per se conventional manner such as extraction with an organic solvent and concentration. When necessary or desired, the product may further be purified by chromatography, distillation, recrystallization, etc.

Other halogenation such as fluorination or bromination and alkylation such as methylation may be carried out by a per se conventional procedure as disclosed in Tetrahedron Letters, 27, 4465 (1986), J.Org.Chem., 32, 2358 (1967), Tetrahedron Letters, 899 (1974), etc.

The thiophenol compound (VI) may be also produced from an aniline compound of the formula:

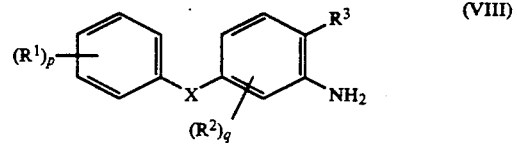

(VIII)

wherein $R^1$, $R^2$, $R^3$, X, p and q are each as defined above according to the method as described in J.Am.Chem.Soc., 72, (1950), Org. Synth., III, 809 (1955), etc.

Further, the phenol compound (VII) and the aniline compound (VIII) can be readily produced from any appropriate commercial product by a conventional procedure.

Some of the starting compounds in the above processes, i.e. the halid (III) and the alcohol (V), are available on the commercial market or can be readily produced from appropriate commercial products by a conventional procedure.

Examples of the aromatic compounds (I) of the present invention are shown in Table 1.

TABLE 1

| $(R^1)_p$ | X | $R^2_q$ | $R^3$ | Y | $R^4$ | $(R^5)_r$ |
|---|---|---|---|---|---|---|
| H | O | H | Cl | O | H | 4-Cl |
| H | O | H | F | O | H | 4-Cl |
| H | O | H | Br | O | H | 4-Cl |
| H | O | H | $CH_3$ | O | H | 4-Cl |
| H | O | H | $C_2H_5$ | O | H | 4-Cl |
| H | O | H | n-$C_3H_7$ | O | H | 4-Cl |
| 3-F | O | H | Cl | O | H | 4-Cl |
| 3-F | O | H | F | O | H | 4-Cl |
| 3-F | O | H | Br | O | H | 4-Cl |
| 3-F | O | H | Cl | O | H | 3,4-$F_2$ |
| 3-F | O | H | Cl | O | H | 4-$CF_3$ |
| 3-F | O | H | $CH_3$ | O | H | 4-Cl |
| 4-F | O | H | Cl | O | H | 4-Cl |
| 4-F | O | H | Br | O | H | 4-Cl |
| 4-F | O | H | F | O | H | 4-Cl |
| 4-F | O | H | $CH_3$ | O | H | 4-Cl |
| 2-F | O | H | Cl | O | H | 4-Cl |
| 2-F | O | H | Br | O | H | 4-Cl |
| 2-F | O | H | F | O | H | 4-Cl |
| 2-F | O | H | $CH_3$ | O | H | 4-Cl |
| 2-Cl | O | H | Cl | O | H | 4-Cl |
| 2-Cl | O | H | Br | O | H | 4-Cl |
| 2-Cl | O | H | F | O | H | 4-Cl |
| 3-F | O | H | Cl | O | H | 4-Br |
| 3-Cl | O | H | Cl | O | H | 4-$CF_3$ |

TABLE 1-continued

| $(R^1)_p$ | X | $R^2_q$ | $R^3$ | Y | $R^4$ | $(R^5)_r$ |
|---|---|---|---|---|---|---|
| 2-Cl | O | H | CH$_3$ | O | H | 4-Cl |
| 3-Cl | O | H | Cl | O | H | 4-Cl |
| 3-Cl | O | H | Br | O | H | 4-Cl |
| 3-Cl | O | H | F | O | H | 4-Cl |
| 3-Cl | O | H | CH$_3$ | O | H | 4-Cl |
| 4-Cl | O | H | Cl | O | H | 4-Cl |
| 4-Cl | O | H | Br | O | H | 4-Cl |
| 4-Cl | O | H | F | O | H | 4-Cl |
| 4-Cl | O | H | CH$_3$ | O | H | 4-Cl |
| 3-Br | O | H | Cl | O | H | 4-Cl |
| 3-Br | O | H | Br | O | H | 4-Cl |
| 3-Br | O | H | F | O | H | 4-Cl |
| 3-Cl | O | H | Cl | O | H | 4-Br |
| 3-Br | O | H | CH$_3$ | O | H | 4-Cl |
| 4-Br | O | H | Cl | O | H | 4-Cl |
| 4-Br | O | H | Br | O | H | 4-Cl |
| 4-Br | O | H | F | O | H | 4-Cl |
| 4-Br | O | H | CH$_3$ | O | H | 4-Cl |
| 2-Br | O | H | Cl | O | H | 4-Cl |
| 2-Br | O | H | Br | O | H | 4-Cl |
| 2-Br | O | H | F | O | H | 4-Cl |
| 2-Br | O | H | CH$_3$ | O | H | 4-Cl |
| 4-I | O | H | Cl | O | H | 4-Cl |
| 4-I | O | H | Br | O | H | 4-Cl |
| 4-I | O | H | F | O | H | 4-Cl |
| 4-I | O | H | CH$_3$ | O | H | 4-Cl |
| 3-I | O | H | Cl | O | H | 4-Cl |
| 3-I | O | H | Br | O | H | 4-Cl |
| 3-I | O | H | F | O | H | 4-Cl |
| 3-I | O | H | CH$_3$ | O | H | 4-Cl |
| 3-CH$_3$ | O | H | Cl | O | H | 4-Cl |
| 3-CH$_3$ | O | H | Br | O | H | 4-Cl |
| 3-CH$_3$ | O | H | F | O | H | 4-Cl |
| 3-CH$_3$ | O | H | CH$_3$ | O | H | 4-Cl |
| 3-C$_2$H$_5$ | O | H | Cl | O | H | 4-Cl |
| 4-CH$_3$ | O | H | Cl | O | H | 4-Cl |
| 4-CH$_3$ | O | H | Br | O | H | 4-Cl |
| 4-CH$_3$ | O | H | F | O | H | 4-Cl |
| 4-CH$_3$ | O | H | CH$_3$ | O | H | 4-Cl |
| 3-CF$_3$ | O | H | Cl | O | H | 4-Cl |
| 3-CF$_3$ | O | H | Br | O | H | 4-Cl |
| 3-CF$_3$ | O | H | F | O | H | 4-Cl |
| 3-CF$_3$ | O | H | CH$_3$ | O | H | 4-Cl |
| 2-C$_2$H$_5$ | O | H | Cl | O | H | 4-Cl |
| 2-NO$_2$ | O | H | Cl | O | H | 4-Cl |
| 2-CF$_3$ | O | H | Cl | O | H | 4-Cl |
| 3-OCH$_3$ | O | H | Cl | O | H | 4-Cl |
| 4-OCHF$_2$ | O | H | Cl | O | H | 4-Cl |
| 4-C$_2$H$_5$ | O | H | Cl | O | H | 4-Cl |
| 3-CN | O | H | Cl | O | H | 4-Cl |
| 4-CF$_3$ | O | H | Cl | O | H | 4-Cl |
| 4-CF$_3$ | O | H | Br | O | H | 4-Cl |
| 4-CF$_3$ | O | H | F | O | H | 4-Cl |
| 4-CF$_3$ | O | H | CH$_3$ | O | H | 4-Cl |
| 4-(iso)C$_3$H$_7$ | O | H | Cl | O | H | 4-Cl |
| 4-(n)C$_4$H$_9$ | O | H | Cl | O | H | 4-Cl |
| 4-OCH$_3$ | O | H | Cl | O | H | 4-Cl |
| 3-NO$_2$ | O | H | Cl | O | H | 4-Cl |
| 4-CN | O | H | Cl | O | H | 4-Cl |
| 4-NO$_2$ | O | H | Cl | O | H | 4-Cl |
| H | \C=O/ | H | Cl | O | H | 4-Cl |
| H | NH | H | Cl | O | H | 4-Cl |
| H | S | H | Cl | O | H | 4-Cl |

TABLE 1-continued

| (R¹)ₚ | X | R²q | R³ | Y | R⁴ | (R⁵)ᵣ |
|---|---|---|---|---|---|---|
| H | \S=O (dimethyl sulfoxide-like) | H | Cl | O | H | 4-Cl |
| H | S(=O)₂ | H | Cl | O | H | 4-Cl |
| H | CH₂ | H | Cl | O | H | 4-Cl |
| H | CH₂ | H | Cl | O | H | 4-CH₃ |
| H | O | H | Cl | S | H | 4-Cl |
| H | O | H | Cl | S | H | 4-CH₃ |
| H | O | H | Cl | O | H | 2,4-Cl₂ |
| H | O | H | Cl | O | H | 3-Cl |
| H | O | H | Cl | O | H | 2,4-Cl₂ |
| H | O | H | Cl | O | H | 4-CH₃ |
| H | O | H | Br | O | H | 4-CH₃ |
| H | O | H | F | O | H | 4-CH₃ |
| H | O | H | CH₃ | O | H | 4-CH₃ |
| H | O | H | C₂H₅ | O | H | 4-CH₃ |
| H | O | H | (n)C₃H₇ | O | H | 4-CH₃ |
| 3-F | O | H | Cl | O | H | 4-CH₃ |
| 3-F | O | H | Br | O | H | 4-CH₃ |
| 3-F | O | H | F | O | H | 4-CH₃ |
| 3-F | O | H | CH₃ | O | H | 4-CH₃ |
| 4-F | O | H | Cl | O | H | 4-CH₃ |
| 4-F | O | H | Br | O | H | 4-CH₃ |
| 4-F | O | H | F | O | H | 4-CH₃ |
| 4-F | O | H | CH₃ | O | H | 4-CH₃ |
| 2-F | O | H | Cl | O | H | 4-CH₃ |
| 3-Cl | O | H | Cl | O | H | 4-CH₃ |
| 3-Cl | O | H | Br | O | H | 4-CH₃ |
| 3-Cl | O | H | F | O | H | 4-CH₃ |
| 3-Cl | O | H | CH₃ | O | H | 4-CH₃ |
| 4-Cl | O | H | Cl | O | H | 4-CH₃ |
| 4-Cl | O | H | Br | O | H | 4-CH₃ |
| 4-Cl | O | H | F | O | H | 4-CH₃ |
| 4-Cl | O | H | CH₃ | O | H | 4-CH₃ |
| 2-Cl | O | H | Cl | O | H | 4-CH₃ |
| 2-Br | O | H | Cl | O | H | 4-CH₃ |
| 3-Br | O | H | Cl | O | H | 4-CH₃ |
| 4-Br | O | H | Cl | O | H | 4-CH₃ |
| 4-I | O | H | Cl | O | H | 4-CH₃ |
| 4-I | O | H | Br | O | H | 4-CH₃ |
| 4-I | O | H | F | O | H | 4-CH₃ |
| 4-I | O | H | CH₃ | O | H | 4-CH₃ |
| 3-I | O | H | Cl | O | H | 4-CH₃ |
| 3-I | O | H | Br | O | H | 4-CH₃ |
| 3-I | O | H | F | O | H | 4-CH₃ |
| 3-I | O | H | CH₃ | O | H | 4-CH₃ |
| 3-CH₃ | O | H | Cl | O | H | 4-CH₃ |
| 3-CH₃ | O | H | Br | O | H | 4-CH₃ |
| 3-CH₃ | O | H | F | O | H | 4-CH₃ |
| 3-CH₃ | O | H | CH₃ | O | H | 4-CH₃ |
| 4-CH₃ | O | H | Cl | O | H | 4-CH₃ |
| 4-CH₃ | O | H | F | O | H | 4-CH₃ |
| 4-CH₃ | O | H | Br | O | H | 4-CH₃ |
| 4-CH₃ | O | H | CH₃ | O | H | 4-CH₃ |
| 3-CF₃ | O | H | Cl | O | H | 4-CH₃ |
| 3-CF₃ | O | H | Br | O | H | 4-CH₃ |
| 3-CF₃ | O | H | F | O | H | 4-CH₃ |
| 3-CF₃ | O | H | CH₃ | O | H | 4-CH₃ |
| 2-CH₃ | O | H | Cl | O | H | 4-CH₃ |
| 3-OCH₃ | O | H | Cl | O | H | 4-CH₃ |
| 4-CF₃ | O | H | Cl | O | H | 4-CH₃ |
| 2-CH₃ | O | H | Cl | O | H | 2-Cl |
| 3,5-F₂ | O | H | Cl | O | H | 4-CF₃ |
| 3,5-F₂ | O | H | Cl | O | H | 4-Br |

TABLE 1-continued

| (R¹)ₚ | X | R²_q | R³ | Y | R⁴ | (R⁵)ᵣ |
|---|---|---|---|---|---|---|
| 3,5-F₂ | O | H | Cl | O | H | 4-Cl |
| 3,5-F₂ | O | H | Br | O | H | 4-Cl |
| 3,5-F₂ | O | H | F | O | H | 4-Cl |
| 3,5-F₂ | O | H | CH₃ | O | H | 4-Cl |
| 2,4-F₂ | O | H | Cl | O | H | 4-Cl |
| 2,4-F₂ | O | H | Br | O | H | 4-Cl |
| 2,4-F₂ | O | H | F | O | H | 4-Cl |
| 2,4-F₂ | O | H | CH₃ | O | H | 4-Cl |
| 3,4-F₂ | O | H | Cl | O | H | 4-Cl |
| 3,4-F₂ | O | H | Br | O | H | 4-Cl |
| 3,4-F₂ | O | H | F | O | H | 4-Cl |
| 3,4-F₂ | O | H | CH₃ | O | H | 4-Cl |
| 2,6-F₂ | O | H | Cl | O | H | 4-Cl |
| 2,6-F₂ | O | H | F | O | H | 4-Cl |
| 2,6-F₂ | O | H | Br | O | H | 4-Cl |
| 2,6-F₂ | O | H | CH₃ | O | H | 4-Cl |
| 2,5-F₂ | O | H | Cl | O | H | 4-Cl |
| 2,5-F₂ | O | H | Br | O | H | 4-Cl |
| 2,5-F₂ | O | H | F | O | H | 4-Cl |
| 2,5-F₂ | O | H | CH₃ | O | H | 4-Cl |
| 2,3-F₂ | O | H | Cl | O | H | 4-Cl |
| 2,3-F₂ | O | H | Br | O | H | 4-Cl |
| 2,3-F₂ | O | H | F | O | H | 4-Cl |
| 2,3-F₂ | O | H | CH₃ | O | H | 4-Cl |
| 3,4-Cl₂ | O | H | Cl | O | H | 4-CF₃ |
| 3,4-Cl₂ | O | H | Cl | O | H | 4-Br |
| 3,4-Cl₂ | O | H | Cl | O | H | 4-Cl |
| 3,4-Cl₂ | O | H | Br | O | H | 4-Cl |
| 3,4-Cl₂ | O | H | F | O | H | 4-Cl |
| 3,4-Cl₂ | O | H | CH₃ | O | H | 4-Cl |
| 3,5-Cl₂ | O | H | F | O | H | 4-Cl |
| 3,5-Cl₂ | O | H | Cl | O | H | 4-Cl |
| 3,5-Cl₂ | O | H | Br | O | H | 4-Cl |
| 3,5-Cl₂ | O | H | CH₃ | O | H | 4-Cl |
| 2,4-Cl₂ | O | H | Cl | O | H | 4-Cl |
| 2,4-Cl₂ | O | H | F | O | H | 4-Cl |
| 2,4-Cl₂ | O | H | Br | O | H | 4-Cl |
| 2,4-Cl₂ | O | H | CH₃ | O | H | 4-Cl |
| 2,5-Cl₂ | O | H | Cl | O | H | 4-Cl |
| 2,5-Cl₂ | O | H | F | O | H | 4-Cl |
| 2,5-Cl₂ | O | H | Br | O | H | 4-Cl |
| 2,5-Cl₂ | O | H | CH₃ | O | H | 4-Cl |
| 2,3-Cl₂ | O | H | Cl | O | H | 4-Cl |
| 2,3-Cl₂ | O | H | F | O | H | 4-Cl |
| 2,3-Cl₂ | O | H | Br | O | H | 4-Cl |
| 2,3-Cl₂ | O | H | CH₃ | O | H | 4-Cl |
| 3,5-Br₂ | O | H | Cl | O | H | 4-Cl |
| 3,5-Br₂ | O | H | F | O | H | 4-Cl |
| 3,5-Br₂ | O | H | Br | O | H | 4-Cl |
| 3,5-Br₂ | O | H | CH₃ | O | H | 4-Cl |
| 2,3-Br₂ | O | H | CH₃ | O | H | 4-Cl |
| 2,3-Br₂ | O | H | Cl | O | H | 4-Cl |
| 2,3-Br₂ | O | H | Br | O | H | 4-Cl |
| 2,3-Br₂ | O | H | F | O | H | 4-Cl |
| 2,5-Br₂ | O | H | Cl | O | H | 4-Cl |
| 2,5-Br₂ | O | H | Br | O | H | 4-Cl |
| 2,5-Br₂ | O | H | F | O | H | 4-Cl |
| 2,5-Br₂ | O | H | CH₃ | O | H | 4-Cl |
| 3,4(CH₃)₂ | O | H | Cl | O | H | 4-Cl |
| 3,4(CH₃)₂ | O | H | F | O | H | 4-Cl |
| 3,4(CH₃)₂ | O | H | Br | O | H | 4-Cl |
| 3,4(CH₃)₂ | O | H | CH₃ | O | H | 4-Cl |
| 3,5(CH₃)₂ | O | H | Cl | O | H | 4-Cl |
| 3,5(CH₃)₂ | O | H | Br | O | H | 4-Cl |
| 3,5(CH₃)₂ | O | H | F | O | H | 4-Cl |
| 3,5(CH₃)₂ | O | H | CH₃ | O | H | 4-Cl |
| 2,5(CH₃)₂ | O | H | Cl | O | H | 4-Cl |
| 2,5(CH₃)₂ | O | H | F | O | H | 4-Cl |
| 2,5(CH₃)₂ | O | H | Br | O | H | 4-Cl |
| 2,5(CH₃)₂ | O | H | CH₃ | O | H | 4-Cl |
| 2,3(CH₃)₂ | O | H | Cl | O | H | 4-Cl |
| 2,3-(CH₃)₂ | O | H | F | O | H | 4-Cl |

TABLE 1-continued

| $(R^1)_p$ | X | $R^2_q$ | $R^3$ | Y | $R^4$ | $(R^5)_r$ |
|---|---|---|---|---|---|---|
| 2,3-(CH₃)₂ | O | H | Br | O | H | 4-Cl |
| 2,3-(CH₃)₂ | O | H | CH₃ | O | H | 4-Cl |
| 2,3-Br₂ | O | H | CH₃ | O | H | 4-Cl |
| 2,3-Br₂ | O | H | Cl | O | H | 4-Cl |
| 2,3-Br₂ | O | H | Br | O | H | 4-Cl |
| 2,3-Br₂ | O | H | F | O | H | 4-Cl |
| 2,5-Br₂ | O | H | Cl | O | H | 4-Cl |
| 2,5-Br₂ | O | H | Br | O | H | 4-Cl |
| 2,5-Br₂ | O | H | F | O | H | 4-Cl |
| 2,5-Br₂ | O | H | CH₃ | O | H | 4-Cl |
| 3,4-(CH₃)₂ | O | H | Cl | O | H | 4-Cl |
| 3,4-(CH₃)₂ | O | H | F | O | H | 4-Cl |
| 3,4-(CH₃)₂ | O | H | Br | O | H | 4-Cl |
| 3,4-(CH₃)₂ | O | H | CH₃ | O | H | 4-Cl |
| 3,5-(CF₃)₂ | O | H | Cl | O | H | 4-Cl |
| 3,5-(CF₃)₂ | O | H | F | O | H | 4-Cl |
| 3,5-(CF₃)₂ | O | H | Br | O | H | 4-Cl |
| 3,5-(CF₃)₂ | O | H | CH₃ | O | H | 4-Cl |
| 3,4,5-Cl₃ | O | H | Cl | O | H | 4-Cl |
| 3,4,5-Cl₃ | O | H | F | O | H | 4-Cl |
| 3,4,5-Cl₃ | O | H | Br | O | H | 4-Cl |
| 3,4,5-Cl₃ | O | H | CH₃ | O | H | 4-Cl |
| 2-F, 4-Cl | O | H | Cl | O | H | 4-Cl |
| 2-F, 4-Cl | O | H | F | O | H | 4-Cl |
| 2-F, 4-Cl | O | H | Br | O | H | 4-Cl |
| 2-F, 4-Cl | O | H | CH₃ | O | H | 4-Cl |
| 2-Cl, 4-Br | O | H | Cl | O | H | 4-Cl |
| 2-Cl, 4-Br | O | H | F | O | H | 4-Cl |
| 2-Cl, 4-Br | O | H | Br | O | H | 4-Cl |
| 2-Cl, 4-Br | O | H | CH₃ | O | H | 4-Cl |
| 2-Cl, 4-CH₃ | O | H | Cl | O | H | 4-Cl |
| 2-Cl, 4-CH₃ | O | H | F | O | H | 4-Cl |
| 2-Cl, 4-CH₃ | O | H | Br | O | H | 4-Cl |
| 2-Cl, 4-CH₃ | O | H | CH₃ | O | H | 4-Cl |
| 2-F, 4-CH₃ | O | H | Cl | O | H | 4-Cl |
| 2-F, 4-CH₃ | O | H | F | O | H | 4-Cl |
| 2-F, 4-CH₃ | O | H | Br | O | H | 4-Cl |
| 2-F, 4-CH₃ | O | H | CH₃ | O | H | 4-Cl |
| 2,4-Br₂ | O | H | Cl | O | H | 4-Cl |
| 2,4-Br₂ | O | H | F | O | H | 4-Cl |
| 2,4-Br₂ | O | H | Br | O | H | 4-Cl |
| 2,4-Br₂ | O | H | CH₃ | O | H | 4-Cl |
| 2-F, 4-Br | O | H | Cl | O | H | 4-Cl |
| 2-F, 4-Br | O | H | F | O | H | 4-Cl |
| 2-F, 4-Br | O | H | Br | O | H | 4-Cl |
| 2-F, 4-Br | O | H | CH₃ | O | H | 4-Cl |
| 2-Cl, 4-CF₃ | O | H | Cl | O | H | 4-Cl |
| 2-Cl, 4-CF₃ | O | H | F | O | H | 4-Cl |
| 2-Cl, 4-CF₃ | O | H | Br | O | H | 4-Cl |
| 2-Cl, 4-CF₃ | O | H | CH₃ | O | H | 4-Cl |
| 2-Cl, 4-F | O | H | Cl | O | H | 4-Cl |
| 2-Cl, 4-F | O | H | F | O | H | 4-Cl |
| 2-Cl, 4-F | O | H | Br | O | H | 4-Cl |
| 2-Cl, 4-F | O | H | CH₃ | O | H | 4-Cl |
| 2-CF₃, 4-Cl | O | H | Cl | O | H | 4-Cl |
| 2-CF₃, 4-Cl | O | H | F | O | H | 4-Cl |
| 2-CF₃, 4-Cl | O | H | Br | O | H | 4-Cl |
| 2-CF₃, 4-Cl | O | H | CH₃ | O | H | 4-Cl |
| 2-CH₃, 4-Cl | O | H | F | O | H | 4-Cl |
| 2-CH₃, 4-Cl | O | H | Cl | O | H | 4-Cl |
| 2-CH₃, 4-Cl | O | H | Br | O | H | 4-Cl |
| 2-CH₃, 4-Cl | O | H | CH₃ | O | H | 4-Cl |
| 2-Br, 4-CH₃ | O | H | Cl | O | H | 4-Cl |
| 2-Br, 4-CH₃ | O | H | F | O | H | 4-Cl |
| 2-Br, 4-CH₃ | O | H | Br | O | H | 4-Cl |
| 2-Br, 4-CH₃ | O | H | CH₃ | O | H | 4-Cl |
| 3-F, 4-CH₃ | O | H | Cl | O | H | 4-Cl |
| 3-F, 4-CH₃ | O | H | F | O | H | 4-Cl |
| 3-F, 4-CH₃ | O | H | Br | O | H | 4-Cl |
| 3-F, 4-CH₃ | O | H | CH₃ | O | H | 4-Cl |
| 3-Cl, 4-CH₃ | O | H | Cl | O | H | 4-Cl |
| 3-Cl, 4-CH₃ | O | H | F | O | H | 4-Cl |

TABLE 1-continued

| (R¹)ₚ | X | R²_q | R³ | Y | R⁴ | (R⁵)ᵣ |
|---|---|---|---|---|---|---|
| 3-Cl, 4-CH₃ | O | H | Br | O | H | 4-Cl |
| 3-Cl, 4-CH₃ | O | H | CH₃ | O | H | 4-Cl |
| 3-Br, 4-CH₃ | O | H | F | O | H | 4-Cl |
| 3-Br, 4-CH₃ | O | H | Cl | O | H | 4-Cl |
| 3-Br, 4-CH₃ | O | H | Br | O | H | 4-Cl |
| 3-Br, 4-CH₃ | O | H | CH₃ | O | H | 4-Cl |
| 3-CH₃, 4-F | O | H | Cl | O | H | 4-Cl |
| 3-CH₃, 4-F | O | H | F | O | H | 4-Cl |
| 3-CH₃, 4-F | O | H | Br | O | H | 4-Cl |
| 3-CH₃, 4-F | O | H | CH₃ | O | H | 4-Cl |
| 3-CH₃, 4-Br | O | H | Cl | O | H | 4-Cl |
| 3-CH₃, 4-Br | O | H | F | O | H | 4-Cl |
| 3-CH₃, 4-Br | O | H | Br | O | H | 4-Cl |
| 3-CH₃, 4-Br | O | H | CH₃ | O | H | 4-Cl |
| 3-Cl, 4-F | O | H | Cl | O | H | 4-Cl |
| 3-Cl, 4-F | O | H | F | O | H | 4-Cl |
| 3-Cl, 4-F | O | H | Br | O | H | 4-Cl |
| 3-Cl, 4-F | O | H | CH₃ | O | H | 4-Cl |
| 3-F, 4-Cl | O | H | Cl | O | H | 4-Cl |
| 3-F, 4-Cl | O | H | F | O | H | 4-Cl |
| 3-F, 4-Cl | O | H | Br | O | H | 4-Cl |
| 3-F, 4-Cl | O | H | CH₃ | O | H | 4-Cl |
| 3-F, 4-Br | O | H | Cl | O | H | 4-Cl |
| 3-F, 4-Br | O | H | F | O | H | 4-Cl |
| 3-F, 4-Br | O | H | Br | O | H | 4-Cl |
| 3-F, 4-Br | O | H | CH₃ | O | H | 4-Cl |
| 3-Cl, 4-Br | O | H | Cl | O | H | 4-Cl |
| 3-Cl, 4-Br | O | H | F | O | H | 4-Cl |
| 3-Cl, 4-Br | O | H | Br | O | H | 4-Cl |
| 3-Cl, 4-Br | O | H | CH₃ | O | H | 4-Cl |
| 3-CF₃, 4-Cl | O | H | Cl | O | H | 4-Cl |
| 3-CF₃, 4-Cl | O | H | F | O | H | 4-Cl |
| 3-CF₃, 4-Cl | O | H | Br | O | H | 4-Cl |
| 3-CF₃, 4-Cl | O | H | CH₃ | O | H | 4-Cl |
| 3-NO₂, 4-Cl | O | H | F | O | H | 4-Cl |
| 3-NO₂, 4-Cl | O | H | Cl | O | H | 4-Cl |
| 3-NO₂, 4-Cl | O | H | Br | O | H | 4-Cl |
| 3-NO₂, 4-Cl | O | H | CH₃ | O | H | 4-Cl |
| 2-Cl, 5-CH₃ | O | H | Cl | O | H | 4-Cl |
| 2-Cl, 5-CH₃ | O | H | F | O | H | 4-Cl |
| 2-Cl, 5-CH₃ | O | H | Br | O | H | 4-Cl |
| 2-Cl, 5-CH₃ | O | H | CH₃ | O | H | 4-Cl |
| 2-F, 5-CH₃ | O | H | Cl | O | H | 4-Cl |
| 2-F, 5-CH₃ | O | H | F | O | H | 4-Cl |
| 2-F, 5-CH₃ | O | H | Br | O | H | 4-Cl |
| 2-F, 5-CH₃ | O | H | CH₃ | O | H | 4-Cl |
| 3-CH₃, 4-Cl | O | H | F | O | H | 4-Cl |
| 3-CH₃, 4-Cl | O | H | Cl | O | H | 4-Cl |
| 3-CH₃, 4-Cl | O | H | Br | O | H | 4-Cl |
| 3-CH₃, 4-Cl | O | H | CH₃ | O | H | 4-Cl |
| 3,5-(CH₃)₂, 4-Cl | O | H | F | O | H | 4-Cl |
| 3,5-(CH₃)₂, 4-Cl | O | H | Cl | O | H | 4-Cl |
| 3,5-(CH₃)₂, 4-Cl | O | H | Br | O | H | 4-Cl |
| 3,5-(CH₃)₂, 4-Cl | O | H | CH₃ | O | H | 4-Cl |
| 2,3,4-Cl₃ | O | H | Cl | O | H | 4-Cl |
| 2,3,4-Cl₃ | O | H | F | O | H | 4-Cl |
| 2,3,4-Cl₃ | O | H | Br | O | H | 4-Cl |
| 2,3,4-Cl₃ | O | H | CH₃ | O | H | 4-Cl |
| 2,4,5-Cl₃ | O | H | Cl | O | H | 4-Cl |
| 2,4,5-Cl₃ | O | H | F | O | H | 4-Cl |
| 2,4,5-Cl₃ | O | H | Br | O | H | 4-Cl |
| 2,4,5-Cl₃ | O | H | CH₃ | O | H | 4-Cl |
| 2,4,6-Cl₃ | O | H | Cl | O | H | 4-Cl |
| 2,4-Cl₂, 3,5-(CH₃)₂ | O | H | Cl | O | H | 4-Cl |
| 2,3,5,6-F₄ | O | H | Cl | O | H | 4-Cl |
| 2,3,4,5,6-F₅ | O | H | Cl | O | H | 4-Cl |
| 3,5-F₂ | O | H | Cl | O | H | 4-CH₃ |
| 3,5-F₂ | O | H | F | O | H | 4-CH₃ |
| 3,5-F₂ | O | H | Br | O | H | 4-CH₃ |
| 3,5-F₂ | O | H | CH₃ | O | H | 4-CH₃ |
| 3,4-Cl₂ | O | H | F | O | H | 4-CH₃ |
| 3,4-Cl₂ | O | H | Cl | O | H | 4-CH₃ |

TABLE 1-continued

| $(R^1)_p$ | X | $R^2_q$ | $R^3$ | Y | $R^4$ | $(R^5)_r$ |
|---|---|---|---|---|---|---|
| 3,4-Cl$_2$ | O | H | Br | O | H | 4-CH$_3$ |
| 3,4-Cl$_2$ | O | H | CH$_3$ | O | H | 4-CH$_3$ |
| 3,5-Cl$_2$ | O | H | Cl | O | H | 4-CH$_3$ |
| 3,5-Cl$_2$ | O | H | F | O | H | 4-CH$_3$ |
| 3,5-Cl$_2$ | O | H | Br | O | H | 4-CH$_3$ |
| 3,5-Cl$_2$ | O | H | CH$_3$ | O | H | 4-CH$_3$ |
| 2,4-F$_2$ | O | H | Cl | O | H | 4-CH$_3$ |
| 2,4-F$_2$ | O | H | Br | O | H | 4-CH$_3$ |
| 2,4-F$_2$ | O | H | F | O | H | 4-CH$_3$ |
| 2,4-F$_2$ | O | H | CH$_3$ | O | H | 4-CH$_3$ |
| 3,4-F$_2$ | O | H | Cl | O | H | 4-CH$_3$ |
| 3,4-F$_2$ | O | H | F | O | H | 4-CH$_3$ |
| 3,4-F$_2$ | O | H | Br | O | H | 4-CH$_3$ |
| 3,4-F$_2$ | O | H | CH$_3$ | O | H | 4-CH$_3$ |
| 2,4-Cl$_2$ | O | H | Cl | O | H | 4-CH$_3$ |
| 2,4-Cl$_2$ | O | H | F | O | H | 4-CH$_3$ |
| 2,4-Cl$_2$ | O | H | Br | O | H | 4-CH$_3$ |
| 2,4-Cl$_2$ | O | H | CH$_3$ | O | H | 4-CH$_3$ |
| 3,5-(CH$_3$)$_2$ | O | H | Cl | O | H | 4-CH$_3$ |
| 3,5-(CH$_3$)$_2$ | O | H | F | O | H | 4-CH$_3$ |
| 3,5-(CH$_3$)$_2$ | O | H | Br | O | H | 4-CH$_3$ |
| 3,5-(CH$_3$)$_2$ | O | H | CH$_3$ | O | H | 4-CH$_3$ |
| 3,4-(CH$_3$)$_2$ | O | H | Cl | O | H | 4-CH$_3$ |
| 3,4-(CH$_3$)$_2$ | O | H | F | O | H | 4-CH$_3$ |
| 3,4-(CH$_3$)$_2$ | O | H | Br | O | H | 4-CH$_3$ |
| 3,4-(CH$_3$)$_2$ | O | H | CH$_3$ | O | H | 4-CH$_3$ |
| 3,5-Br$_2$ | O | H | Cl | O | H | 4-CH$_3$ |
| 2,6-F$_2$ | O | H | Cl | O | H | 4-CH$_3$ |
| 2,5-Cl$_2$ | O | H | Cl | O | H | 4-CH$_3$ |
| 2,5-F$_2$ | O | H | Cl | O | H | 4-CH$_3$ |
| 2,5-F$_2$ | O | H | F | O | H | 4-CH$_3$ |
| 2,5-F$_2$ | O | H | Br | O | H | 4-CH$_3$ |
| 2,5-F$_2$ | O | H | CH$_3$ | O | H | 4-CH$_3$ |
| 2,3-F$_2$ | O | H | Cl | O | H | 4-CH$_3$ |
| 2,3-F$_2$ | O | H | F | O | H | 4-CH$_3$ |
| 2,3-F$_2$ | O | H | Br | O | H | 4-CH$_3$ |
| 2,3-F$_2$ | O | H | CH$_3$ | O | H | 4-CH$_3$ |
| 2,5-(CH$_3$)$_2$ | O | H | Cl | O | H | 4-CH$_3$ |
| 2,3-Cl$_2$ | O | H | Cl | O | H | 4-CH$_3$ |
| 2,3-(CH$_3$)$_2$ | O | H | Cl | O | H | 4-CH$_3$ |
| 2,3-Br$_2$ | O | H | Cl | O | H | 4-CH$_3$ |
| 2,5-Br$_2$ | O | H | Cl | O | H | 4-CH$_3$ |
| 3,5-(CF$_3$)$_2$ | O | H | Cl | O | H | 4-CH$_3$ |
| 3,4,5-Cl$_3$ | O | H | Cl | O | H | 4-CH$_3$ |
| 2-F, 4-Cl | O | H | Cl | O | H | 4-CH$_3$ |
| 2-Cl, 4-Br | O | H | Cl | O | H | 4-CH$_3$ |
| 2-Cl, 4-CH$_3$ | O | H | Cl | O | H | 4-CH$_3$ |
| 2-F, 4-CH$_3$ | O | H | Cl | O | H | 4-CH$_3$ |
| 2,4-Br$_2$ | O | H | Cl | O | H | 4-CH$_3$ |
| 2-F, 4-Br | O | H | Cl | O | H | 4-CH$_3$ |
| 2-Cl, 4-CF$_3$ | O | H | Cl | O | H | 4-CH$_3$ |
| 2-Cl, 4-F | O | H | Cl | O | H | 4-CH$_3$ |
| 2-CF$_3$, 4-Cl | O | H | Cl | O | H | 4-CH$_3$ |
| 2-CH$_3$, 4-Cl | O | H | Cl | O | H | 4-CH$_3$ |
| 2-Br, 4-CH$_3$ | O | H | Cl | O | H | 4-CH$_3$ |
| 3-F, 4-CH$_3$ | O | H | Cl | O | H | 4-CH$_3$ |
| 3-F, 4-CH$_3$ | O | H | F | O | H | 4-CH$_3$ |
| 3-F, 4-CH$_3$ | O | H | Br | O | H | 4-CH$_3$ |
| 3-F, 4-CH$_3$ | O | H | CH$_3$ | O | H | 4-CH$_3$ |
| 3-Cl, 4-CH$_3$ | O | H | F | O | H | 4-CH$_3$ |
| 3-Cl, 4-CH$_3$ | O | H | Cl | O | H | 4-CH$_3$ |
| 3-Cl, 4-CH$_3$ | O | H | Br | O | H | 4-CH$_3$ |
| 3-Cl, 4-CH$_3$ | O | H | CH$_3$ | O | H | 4-CH$_3$ |
| 3-Br, 4-CH$_3$ | O | H | Cl | O | H | 4-CH$_3$ |
| 3-CH$_3$, 4-F | O | H | Cl | O | H | 4-CH$_3$ |
| 3-CH$_3$, 4-Br | O | H | Cl | O | H | 4-CH$_3$ |
| 3-Cl, 4-F | O | H | Cl | O | H | 4-CH$_3$ |
| 3-Cl, 4-F | O | H | Br | O | H | 4-CH$_3$ |
| 3-Cl, 4-F | O | H | F | O | H | 4-CH$_3$ |
| 3-Cl, 4-F | O | H | CH$_3$ | O | H | 4-CH$_3$ |
| 3-F, 4-Cl | O | H | Cl | O | H | 4-CH$_3$ |
| 3-F, 4-Cl | O | H | F | O | H | 4-CH$_3$ |

TABLE 1-continued

| $(R^1)_p$ | X | $R^2_q$ | $R^3$ | Y | $R^4$ | $(R^5)_r$ |
|---|---|---|---|---|---|---|
| 3-F, 4-Cl | O | H | Br | O | H | 4-CH$_3$ |
| 3-F, 4-Cl | O | H | CH$_3$ | O | H | 4-CH$_3$ |
| 3-F, 4-Br | O | H | Cl | O | H | 4-CH$_3$ |
| 3-F, 4-Br | O | H | F | O | H | 4-CH$_3$ |
| 3-F, 4-Br | O | H | Br | O | H | 4-CH$_3$ |
| 3-F, 4-Br | O | H | CH$_3$ | O | H | 4-CH$_3$ |
| 3-Cl, 4-Br | O | H | F | O | H | 4-CH$_3$ |
| 3-Cl, 4-Br | O | H | Cl | O | H | 4-CH$_3$ |
| 3-Cl, 4-Br | O | H | Br | O | H | 4-CH$_3$ |
| 3-Cl, 4-Br | O | H | CH$_3$ | O | H | 4-CH$_3$ |
| 3-CF$_3$, 4-Cl | O | H | Cl | O | H | 4-CH$_3$ |
| 2-Cl, 5-CH$_3$ | O | H | Cl | O | H | 4-CH$_3$ |
| 2-F, 5-CH$_3$ | O | H | Cl | O | H | 4-CH$_3$ |
| 3-CH$_3$, 4-Cl | O | H | Cl | O | H | 4-CH$_3$ |
| 3,4-Br$_2$ | O | H | Cl | O | H | 4-CH$_3$ |
| 3-Cl | O | H | Cl | S | H | 4-Cl |
| 3,4-Cl$_2$ | O | H | Cl | S | H | 4-CH$_3$ |
| 3,5-F$_2$ | O | H | Cl | S | H | 4-Br |
| 3-F | O | H | Cl | S | H | 4-CF$_3$ |
| H | O | H | Cl | S | H | 4-CH$_3$ |
| 3,5-F$_2$ | CH$_2$ | H | Cl | S | H | 4-CH$_3$ |
| 3-Cl | CH$_2$ | H | Cl | S | H | 4-CH$_3$ |
| H | CH$_2$ | H | Cl | S | H | 4-Br |
| 3,5-F$_2$ | O | 4-Cl | Cl | O | H | 4-Cl |
| H | O | 4-Cl | Cl | O | H | 4-Cl |
| H | O | 4-F | Cl | O | H | 4-Cl |
| H | O | 3,4-Cl$_2$ | Cl | O | H | 4-Cl |
| H | O | 3,4-(CH$_3$)$_2$ | Cl | O | H | 4-Cl |
| H | O | 3-Cl | Cl | O | H | 4-Cl |
| H | O | H | Cl | O | CH$_3$ | 4-Cl |
| H | O | H | Cl | O | C$_2$H$_5$ | 4-Cl |
| H | O | H | Cl | O | H | 4-F |
| H | O | H | Cl | O | H | 4-Br |
| H | O | H | Cl | O | H | 4-CF$_3$ |
| H | O | H | Cl | O | H | 4-C$_2$H$_5$ |
| H | O | H | Cl | O | H | 4-(iso)C$_3$H$_7$ |
| H | O | H | Cl | O | H | 4-(n)C$_3$H$_7$ |
| H | O | H | Cl | O | H | 4-I |
| 3-CH$_3$ | CH$_2$ | H | Cl | O | H | 4-CF$_3$ |
| 4-Cl | CH$_2$ | H | Cl | O | H | H |
| 4-Cl | CH$_2$ | H | Cl | O | H | 4-CH$_3$ |
| 4-Cl | CH$_2$ | H | Cl | O | H | 4-C$_2$H$_5$ |
| 4-Cl | CH$_2$ | H | Cl | O | H | 4-Cl |
| 4-Cl | CH$_2$ | H | Cl | O | H | 4-Br |
| 4-Cl | CH$_2$ | H | Cl | O | H | 4-CF$_3$ |
| 3,5-F$_2$ | O | H | Cl | O | CH$_3$ | 4-Cl |
| 3-Cl | O | H | Cl | O | CH$_3$ | 4-Br |
| 3,4-Cl$_2$ | O | H | Cl | O | CH$_3$ | 4-CF$_3$ |
| 3,5-F$_2$ | CH$_2$ | H | Cl | O | CH$_3$ | 4-CH$_3$ |
| 3,4-Cl$_2$ | CH$_2$ | H | Cl | O | CH$_3$ | 4-Cl |
| 3-Cl | CH$_2$ | H | Cl | O | CH$_3$ | 4-Br |
| 3,4-(-O—CH$_2$—O-) | O | H | Cl | O | H | 4-Cl |
| 3,4-(-O—C(CH$_2$)(CH$_3$)—O-) | O | H | Cl | O | H | 4-Cl |
| 3,4-(-O—CH(CH$_3$)—O-) | O | H | Cl | O | H | 4-CH$_3$ |
| 3,4-(-O—CF$_2$—O-) | O | H | Cl | O | H | 4-CH$_3$ |
| 3,4-(-O—CH$_2$—O-) | CH$_2$ | H | Cl | O | H | 4-CH$_3$ |
| H | CH$_2$ | H | Cl | O | H | H |
| H | CH$_2$ | H | Cl | O | H | 4-Br |

TABLE 1-continued

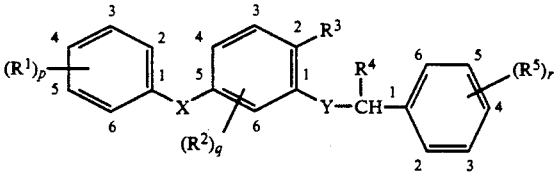

| (R¹)ₚ | X | R²_q | R³ | Y | R⁴ | (R⁵)ᵣ |
|---|---|---|---|---|---|---|
| H | CH₂ | H | Cl | O | H | 4-C₂H₅ |
| H | CH₂ | H | Cl | O | H | 4-(iso)C₃H₇ |
| 2,4-Cl₂ | CH₂ | H | Cl | O | H | H |
| 2,4-Cl₂ | CH₂ | H | Cl | O | H | 4-Cl |
| 2,4-Cl₂ | CH₂ | H | Cl | O | H | 4-CH₃ |
| 2,4-Cl₂ | CH₂ | H | Cl | O | H | 4-C₂H₅ |
| 2,4-Cl₂ | CH₂ | H | Cl | O | H | 4-(iso)C₃H₇ |
| 3,5-F₂ | CH₂ | H | Cl | O | H | H |
| 3,5-F₂ | CH₂ | H | Cl | O | H | 4-Cl |
| 3,5-F₂ | CH₂ | H | Cl | O | H | 4-CH₃ |
| 3,5-F₂ | CH₂ | H | Cl | O | H | 4-C₂H₅ |
| 3,5-F₂ | CH₂ | H | Cl | O | H | 4-(iso)C₃H₇ |
| 3,5-F₂ | CH₂ | H | Cl | O | H | 4-F |
| 3,5-F₂ | CH₂ | H | Cl | O | H | 4-Br |
| 3,5-F₂ | CH₂ | H | Cl | O | H | 4-OCBrF₂ |
| 3,4-Cl₂ | CH₂ | H | Cl | O | H | 4-(iso)C₃H₇ |
| 3,4-Cl₂ | CH₂ | H | Cl | O | H | 4-OCF₂CF₂H |
| 3,4-Cl₂ | CH₂ | H | Cl | O | H | 4-OCBrF₂ |
| 3-F | CH₂ | H | Cl | O | H | H |
| 3-F | CH₂ | H | Cl | O | H | 4-CH₃ |
| 3-F | CH₂ | H | Cl | O | H | 4-Cl |
| 3-F | CH₂ | H | Cl | O | H | 4-F |
| 3-F | CH₂ | H | Cl | O | H | 4-Br |
| 3-F | CH₂ | H | Cl | O | H | 3,4-F₂ |
| 3-F | CH₂ | H | Cl | O | H | 3,5-Cl₂ |
| 3-F | CH₂ | H | Cl | O | H | 4-OCH₃ |
| 3-F | CH₂ | H | Cl | O | H | 3-Cl |
| 3-F | CH₂ | H | Cl | O | H | 2-Cl |
| 3-F | CH₂ | H | Cl | O | H | 4-CH₃ |
| 3-F | CH₂ | H | Cl | O | H | 4-C₂H₅ |
| 3-F | CH₂ | H | Cl | O | H | 4-(iso)C₃H₇ |
| 3-F | CH₂ | H | Cl | O | H | 4-OCF₂CF₂H |
| 3-F | CH₂ | H | Cl | O | H | 4-OCBrF₂ |
| 3,5-F₂ | CH₂ | H | Cl | O | H | 4-OCF₂CF₂H |
| H | CH₂ | H | Cl | O | H | F |
| H | CH₂ | H | Cl | O | H | 4-OCBrF₂ |
| 2,4-F₂ | CH₂ | H | Cl | O | H | H |
| 2,4-F₂ | CH₂ | H | Cl | O | H | 4-Cl |
| 2,4-F₂ | CH₂ | H | Cl | O | H | 4-CH₃ |
| 2,4-F₂ | CH₂ | H | Cl | O | H | 4-F |
| 2,4-F₂ | CH₂ | H | Cl | O | H | 4-Br |
| 2,4-F₂ | CH₂ | H | Cl | O | H | 4-C₂H₅ |
| 2,4-F₂ | CH₂ | H | Cl | O | H | 4-OCBrF₂ |
| 2,4-F₂ | CH₂ | H | Cl | O | H | 4-(iso)C₃H₇ |
| 2,4-F₂ | CH₂ | H | Cl | O | H | 4-OCF₂CF₂H |
| 3,4-Cl₂ | CH₂ | H | Cl | O | H | H |
| 3,4-Cl₂ | CH₂ | H | Cl | O | H | 4-Cl |
| 3,4-Cl₂ | CH₂ | H | Cl | O | H | 4-Br |
| 3,4-Cl₂ | CH₂ | H | Cl | O | H | 4-F |
| 3,4-Cl₂ | CH₂ | H | Cl | O | H | 4-CH₃ |
| 3,4-Cl₂ | CH₂ | H | Cl | O | H | 4-C₂H₅ |
| 3,5-F₂ | CH₂ | H | Cl | O | H | 3-Cl |
| 3,5-F₂ | CH₂ | H | Cl | O | H | 2-Cl |
| 3,5-F₂ | CH₂ | H | Cl | O | H | 3,4-F₂ |
| 3,5-F₂ | CH₂ | H | Cl | O | H | 3,5-Cl₂ |
| 3,5-F₂ | CH₂ | H | Cl | O | H | 3,4-Cl₂ |
| 3-Cl | CH₂ | H | Cl | O | H | H |
| 3-Cl | CH₂ | H | Cl | O | H | 4-Br |
| 3-Cl | CH₂ | H | Cl | O | H | 4-CH₃ |
| 3-Cl | CH₂ | H | Cl | O | H | 4-C₂H₅ |
| 3-Cl | CH₂ | H | Cl | O | H | 4-CF₃ |
| 3-Cl | CH₂ | H | Cl | O | H | 4-Cl |
| 3-Cl | CH₂ | H | Cl | O | H | 4-I |
| 3-Cl | CH₂ | H | Cl | O | H | 3,4-F₂ |
| 3-CH₃ | CH₂ | H | Cl | O | H | H |
| 3-CH₃ | CH₂ | H | Cl | O | H | 4-Br |
| 3-CH₃ | CH₂ | H | Cl | O | H | 4-Cl |
| 3-CH₃ | CH₂ | H | Cl | O | H | 4-CH₃ |
| 3-CH₃ | CH₂ | H | Cl | O | H | 4-C₂H₅ |
| 3-CH₃ | O | 4-Br | Cl | O | H | 4-Cl |
| 3,4-(CH₃)₂ | O | 4-Br | Cl | O | H | 4-Cl |
| 3,5-(CH₃)₂ | O | 4-Br | Cl | O | H | 4-Cl |

TABLE 1-continued

| $(R^1)_p$ | X | $R^2_q$ | $R^3$ | Y | $R^4$ | $(R^5)_r$ |
|---|---|---|---|---|---|---|
| 3-F, 4-CH$_3$ | O | 4-Br | Cl | O | H | 4-Cl |
| 3-Cl, 4-CH$_3$ | O | 4-Br | Cl | O | H | 4-Cl |
| 3-F, 4-Cl | O | 4-Br | Cl | O | H | 4-Cl |
| 3-CH$_3$, 4-Cl | O | 4-Br | Cl | O | H | 4-Cl |
| 2,5-F$_2$ | O | 4-Br | Cl | O | H | 4-Cl |
| 2,3-F$_2$ | O | 4-Br | Cl | O | H | 4-Cl |
| 3-CH$_3$, 4-Cl | O | 4-Br | Cl | O | H | 4-Cl |
| H | O | 4-F | Cl | O | H | 4-Cl |
| 3-F | O | 4-F | Cl | O | H | 4-Cl |
| H | O | 4-CH$_3$ | Cl | O | H | 4-Cl |
| 3-F | O | 4-CH$_3$ | Cl | O | H | 4-Cl |
| 3,5-F$_2$ | O | 4-CH$_3$ | Cl | O | H | 4-Cl |
| 3-Cl | O | 4-CH$_3$ | Cl | O | H | 4-Cl |
| 3,4-Cl$_2$ | O | 4-CH$_3$ | Cl | O | H | 4-Cl |
| 4-Cl | O | 4-CH$_3$ | Cl | O | H | 4-Cl |
| 3,5-Cl$_2$ | O | 4-CH$_3$ | Cl | O | H | 4-Cl |
| 2,4-F$_2$ | O | 4-CH$_3$ | Cl | O | H | 4-Cl |
| 3,4-F$_2$ | O | 4-CH$_3$ | Cl | O | H | 4-Cl |
| 3,5-F$_2$ | O | 4-F | Cl | O | H | 4-Cl |
| 3-Cl | O | 4-F | Cl | O | H | 4-Cl |
| 3,4-Cl$_2$ | O | 4-F | Cl | O | H | 4-Cl |
| 4-Cl | O | 4-F | Cl | O | H | 4-Cl |
| 3,5-Cl$_2$ | O | 4-F | Cl | O | H | 4-Cl |
| 2,4-F$_2$ | O | 4-F | Cl | O | H | 4-Cl |
| 3,4-F$_2$ | O | 4-F | Cl | O | H | 4-Cl |
| 4-F | O | 4-F | Cl | O | H | 4-Cl |
| 3-CH$_3$ | O | 4-F | Cl | O | H | 4-Cl |
| 3,4-(CH$_3$)$_2$ | O | 4-F | Cl | O | H | 4-Cl |
| 3,5-(CH$_3$)$_2$ | O | 4-F | Cl | O | H | 4-Cl |
| 3-F, 4-CH$_3$ | O | 4-F | Cl | O | H | 4-Cl |
| 3-F | O | H | Cl | O | H | 4-I |
| 3,5-F$_2$ | O | H | Cl | O | H | 4-I |
| 3,4-Cl$_2$ | O | H | Cl | O | H | 4-I |
| 3-CH$_3$ | O | H | Cl | O | H | 4-I |
| H | O | H | Cl | O | H | 4-OCH$_3$ |
| H | O | H | Cl | O | H | 4-OC$_2$H$_5$ |
| H | O | H | Cl | O | H | 4-OCF$_3$ |
| H | O | H | Cl | O | H | 4-OCHF$_2$ |
| H | O | 4-Cl | Cl | O | H | 4-Cl |
| 3-F | O | 4-Cl | Cl | O | H | 4-Cl |
| 3,5-F$_2$ | O | 4-Cl | Cl | O | H | 4-Cl |
| 3-Cl | O | 4-Cl | Cl | O | H | 4-Cl |
| 3,4-Cl$_2$ | O | 4-Cl | Cl | O | H | 4-Cl |
| 4-Cl | O | 4-Cl | Cl | O | H | 4-Cl |
| 3,5-Cl$_2$ | O | 4-Cl | Cl | O | H | 4-Cl |
| 2,4-F$_2$ | O | 4-Cl | Cl | O | H | 4-Cl |
| 3,4-F$_2$ | O | 4-Cl | Cl | O | H | 4-Cl |
| 4-F | O | 4-Cl | Cl | O | H | 4-Cl |
| 3-CH$_3$ | O | 4-Cl | Cl | O | H | 4-Cl |
| 3,4-(CH$_3$)$_2$ | O | 4-Cl | Cl | O | H | 4-Cl |
| 3-F, 4-CH$_3$ | O | 4-Cl | Cl | O | H | 4-Cl |
| 3-F, 4-Cl | O | 4-Cl | Cl | O | H | 4-Cl |
| 3-CH$_3$, 4-Cl | O | 4-Cl | Cl | O | H | 4-Cl |
| 2,5-F$_2$ | O | 4-Cl | Cl | O | H | 4-Cl |
| 3,4-F$_2$ | O | 4-Cl | Cl | O | H | 4-Cl |
| 3-CH$_3$, 4-Cl | O | 4-Cl | Cl | O | H | 4-Cl |
| 3,5-F$_2$ | O | H | Cl | O | CH$_3$ | 4-Cl |
| 3,4-(O—CH$_2$—O) | O | H | Cl | O | CH$_3$ | 4-Cl |
| 3,4-(O—CH$_2$—O) | CH$_2$ | H | Cl | O | CH$_3$ | 4-CH$_3$ |
| 3,5-F$_2$ | O | H | Cl | O | C$_2$H$_5$ | 4-Cl |
| 3,4-Cl$_2$ | O | H | Cl | O | CH$_3$ | 4-Cl |
| 3-F | O | H | Cl | O | H | 4-Cl |
| 3,4-F$_2$ | O | H | Cl | O | (iso)C$_3$H$_7$ | 4-Cl |

Examples of the insect pests against which the aromatic compounds (I) of the invention exhibit controlling effects are as shown below.

Hemiptera

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cincticeps*), *Nephotettix virescense, Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (Aleyrodidae) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); Agrothis spp. such as turnip cutworm (*Agrothis segetum*) and black cutworm (*Agrothis ipsilon*); Heliothis spp.; Pieridae such as common cabbageworm (*Pieris rapae crucivora*); tortricid moths (Tortricidae) such as Adoxophyes spp. and Grapholita spp.; Carposinidae such as lyonetiid moths (Lyonetiidae), leafblotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bisselliella*), etc.

Diptera

Mosquitos (Calicidae) such as common mosquito (*Culex pipiens pallens*) and *Culex tritaeniorhynchus*; Aedes spp. such as *Aedes aegypti* and *Aedes albopictus*; Anopheles spp. such as *Anopheles sinensis*; midges (Chironomidae); Muscidae such as housefly (*musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae); etc.

Coleoptera

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red flour beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera

Thrips such as *Thrips palmi*, yellow tea thrips (*Scirtothrips dorsalis*) and flower thrips (*Thrips hawaiiensis*), etc.

Hymenoptera

Ants (Formicidae); sawflies (Tenthredinidae) such as cabbage sawfly (*Athalia rosae ruficornis*), etc.

Orthoptera

Mole crickets (Gryllotalpidae); grasshoppers (Acrididae), etc.

Aphaniptera

*Purex irritans*, etc.

Anoplura

*Pediculus humanus capitis, Phthirus pubis*, etc.

Isoptera

*Reticulitermes speratus*, Formosan subterrauean termite (*Coptotermes formosanus*), etc.

Among the insect pests as above exemplified, the aromatic compounds (I) are particularly effective in controlling those belonging to Hemiptera and also exhibit a remarkable controlling effect on planthoppers and leafhoppers in a field of rice plant.

The aromatic compounds (I) may be used alone as insecticides or in mixtures with other insecticides and/or acaricides to enhance or expand their insecticidal or pesticidal use.

Examples of the other insecticides and/or acaricide include organophosphorus compounds (e.g. fenitrothion (0,0-dimethyl 0-(3-methyl-4-nitrophenyl)phosphorothioate), fenthion (0,0-dimethyl 0-[3-methyl-4-(methylthio)-phenyl]phosphorothioate), diazinon (0,0-diethyl-0-(2-isopropyl-6-methyl-pyrimidin-4-yl)phosphorothioate), chlorpyrifos (0,0-diethyl-0-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl 0,0-dimethylphosphorodithioate), disulfoton (0,0-diethyl S-2-ethylthioethyl phosphorothioate), DDVP (2,2-dichlorovinyldimethylphosphate), sulprofos (0-ethyl 0-4-(methylthio)phenyl S-propyl phosphorodithioate), cyanophos (0-4-cyanophenyl 0,0-dimethyl phosphorothioate), dioxabenzofos · (2-methoxy-4H-1,3,2-benzodioxaphosphinine-2-sulphide), dimethoate (0,0-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl 0,0-dimethylphosphoro-dithioate) and monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethio-fencarb (2-(ethylthiomethyl)phenyl methylcarbamate), aldicarb (2-methyl-2-(methylthio)propionaldehyde 0-methylcarbamoyloxime) and Oxamyl (N,N-dimethyl-2-methylcarbamoyloxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2-dichlorovinyl)-2,2-dimethylcyclopropanecarboxylate), permethrin (3-phenoxybenzyl (1RS,3RS)-(1RS,3RS)-3-(2,2-dichlorovinyl)2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alpha-cyano-m-phenoxybenzyl (1R,3R)-3-(2,2-dibromovinyl)-2-dimethylcyclopropanecarboxylate) and cycloprothrin ((RS)-alpha-cyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triadiazin-4-one), etc.); nitroimidazolidine derivatives (e.g. imidacloprid (1-((6-chloro-3-pyridylmethyl)-N-nitroimidazolidin-2-ylideneamine), etc.); nereistoxin derivatives (e g. cartap (S,S'-(2-dimethylaminotrimethylene) bis(thiocarbamate), thiocyclam (N,N-dimethyl-1,2,3-trithian-5-ylamine) and bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide and gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phehyl]-3-(2,6-difluorobenzoyl)urea), teflubenzuron (1-(3,5-dichloro-2,4-difluorophenyl) 3-(2,6-difluorobenzoyl)urea) and flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)dimethylidyne]di-2,4-xylidine) and chlordimeform (N'-(4-chloro-2-methylphenyl)-N,N-dimethylmethanimidamide), etc.).

On the practical use of the aromatic compounds (I) as insecticides, they may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition of the invention contains generally the aromatic compound(s) (I) as the active ingredient in an amount of from about 0.001 % to 95 % by weight based on the composition.

Examples of the solid carrier usable for making the composition are fine powders or granules of clays (e.g. kaolin clay, diatomaceous earth, synthetic hydrated silica, bentonite, Fubasami clay terra alba), talc, ceramics, other inorganic minerals (e.g. sericite, quartz, sulfur, activated arbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate, etc.), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyacrylic alcohol, polyvinylpyrrolidone, polyacrylic acid), etc. Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reaction-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxyrtolune and nordihydroguaiaretic acid, preservatives such as dehydroacetic acid, feeding error preventing agnets such as red paper powders, incentive flavors such as cheese flavor and onion flavor, etc.

Flowable concentrates (water-based suspension or emulsion formulations) are generally obtained by dispersing about 1 to 75 parts by weight of the aromatic compound (I) as the active ingredient finely and uniformly into water containing about 0.5 to 15 parts by weight of a dispersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anticorrosive agent, a stabilizing agent, a spreading agents, penetration auxiliaries, antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc. Examples of the compounds giving a thixotropic property are bentonite, aluminum magnesium silicate, xanthane gum, polyacrylic acid, etc.

The composition of the invention thus obtained may be used as such or after diluting with water. It may be also used in a mixture with any other active component or composition chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the aromatic compound (I) according to the present invention may be applied to the insect pests or the locus where the insect pests propagate generally in an amount of about 0.001 g to 500 g, and preferably about 0.1 g to 500 g per 10 ares. when the aromatic compound (I) is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the aromatic compound (I) is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

Production Example 1 (Production of Compound No. 9 by Process A)

To a solution of 0.10 g of sodium hydride (60 % oil dispersion) in 10 ml of N,N-dimethylformamide, there was added dropwise a solution of 0.50 g of 2-chloro-5-phenoxyphenol in 3 ml of N,N-dimethylformamide with stirring and ice-cooling. After 30 minutes, a solution of 0.63 g of p-ethylbenzylbromide in 5 ml of N,N-dimethylformamide was added thereto at room temperature, followed by stirring at the same temperature for 12 hours. The reaction mixture was poured into ice-water and extracted twice with ethyl acetate. The extracts were combined together, washed with water, dried over anhydrous magnesium sulfate and concentrated under reduced pressure. The residue was subjected to silica gel chromatography to give 0.70 g of [2-chloro-1-(4-ethylbenzyloxy)-5-phenoxy]benzene. Yield, 91%. $n_D^{23.8}$: 1.5942.

Production Example 2 (Production of Compound No. 17 by Process B)

A mixture of 0.50 g of 2-chloro-5-(3,4-difluorophenoxy)phenol, 0.31 g of 1-(4-chlorophenyl)ethanol, 0.51 g of triphenylphosphine, 0.39 g of diethylazadicarboxylate and 0 ml of anhydrous tetrahydrofuran was stirred at room temperature. After 48 hours, the reaction mixture was concentrated, and 50 ml of diethyl ether were added thereto. The precipitate was removed by filtration, and the filtrate was concentrated. The residue was subjected to silica gel chromatography to give 0.37 g of [2-chloro-1-[1-(4-chlorophenyl)ethoxy]-5-(3,4-difluorophenoxy) ]benzene. Yield, 48 % . $n_D^{22.6}$: 1.5785.

Production Example 3 (Production of Compound No. 18 by Process A)

To a solution of 0.09 g of sodium hydride (60 % oil dispersion) in 10 ml of N,N-dimethylformamide, there is added dropwise a solution of 0.50 g of 2-methyl-5-(3,5-difluorophenoxy)phenol in 3 ml of N,N-dimethylformamide with stirring and ice-cooling. After 30 minutes, a solution of 0.34 g of p-chlorobenzylchloride in 5 ml of N,N-dimethylformamide is added thereto at room temperature, followed by stirring at the same temperature for 12 hours. The reaction mixture is poured into ice-water and extracted twice with ethyl acetate. The extracts are combined together, washed with water, dried over anhydrous magnesium sulfate and concentrated under reduced pressure. The residue is subjected to silica gel chromatography to give [1-(4-chlorobenzyloxy)-5-(3-chlorophenoxy)-2-methyl]benzene.

Production Example 4 (Production of Compound No. 19 by Process A)

To a solution of 0.07 g of sodium hydride (60 % oil dispersion) in 10 ml of N,N-dimethylformamide, there is added dropwise a solution of 0.50 g of 2-bromo-5-(3-chlorophenoxy)phenol in 3 ml of N,N-dimethylformamide with stirring and ice-cooling. After 30 minutes, a solution of 0.27 g of p-chlorobenzylchloride in 5 ml of N,N-dimethylformamide is added thereto at room temperature, followed by stirring at the same temperature for 12 hours. The reaction mixture is poured into ice-water and extracted twice with ethyl acetate. The extracts are combined together, washed with water, dried over anhydrous magnesium sulfate and concentrated under reduced pressure. The residue is subjected to silica gel chromatography to give [2-bromo-1-(4-chlorobenzyloxy)-5-(3-chlorophenoxy)]benzene.

Production Example 5 (Production of Compound No. 20 by Process A)

To a solution of 0.09 g of sodium hydride (60 % oil dispersion) in 10 ml of N,N-dimethylformamide, there is added dropwise a solution of 0.50 g of 5-benzyl-2-chlorophenol in 3 ml of N,N-dimethylformamide with stirring and ice-cooling. After 30 minutes, a solution of 0.35 g of p-ethylbenzylchloride in 5 ml of N,N-dimethylformamide is added thereto at room temperature, followed by stirring at the same temperature for 12 hours. The reaction mixture is poured into ice-water and extracted twice with ethyl acetate. The extracts are combined together, washed with water, dried over anhydrous magnesium sulfate and concentrated under reduced pressure. The residue is subjected to silica gel chromatography to give [5-benzyl-2-chloro-1-(4-ethylbenzyloxy)]benzene.

Some examples of the aromatic compounds (I) as produced in the same manner as above are shown in Table 2.

TABLE 2

| Compound No. | Chemical structure | Physical constant |
|---|---|---|
| 1 | (structure) | $n_D^{24.5}$: 1.6111 |
| 2 | (structure) | $n_D^{24.4}$: 1.6221 |
| 3 | (structure) | $n_D^{22.0}$: 1.5851 |
| 4 | (structure) | m.p., 115.9° C. |
| 5 | (structure) | $n_D^{24.3}$: 1.6031 |
| 6 | (structure) | $n_D^{23.1}$: 1.5766 |
| 7 | (structure) | $n_D^{24.9}$: 1.5622 |
| 8 | (structure) | $n_D^{22.5}$: 1.5738 |

TABLE 2-continued

| Compound No. | Chemical structure | Physical constant |
|---|---|---|
| 9 | (phenyl)-O-(2-chloro-5-phenoxyphenyl)-O-CH(H)-(4-ethylphenyl) | $n_D^{23.8}$: 1.5942 |
| 10 | (3,4-dichlorophenyl)-O-(2-chloro-5-phenoxyphenyl)-O-CH(H)-(4-chlorophenyl) | m.p., 90.4° C. |
| 11 | (3,5-difluorophenyl)-O-(2-chloro-5-phenoxyphenyl)-O-CH(H)-(4-chlorophenyl) | $n_D^{23.1}$: 1.5881 |
| 12 | (3,4-dichlorophenyl)-O-(2-chloro-5-phenoxyphenyl)-O-CH(H)-(4-methylphenyl) | $n_D^{23.1}$ 1.6112 |
| 13 | (3,4-dichlorophenyl)-O-(4,5-dichlorophenyl)-O-CH(H)-(4-chlorophenyl) | m.p., 96.5° C. |
| 14 | (3,5-difluorophenyl)-O-(4,5-dichlorophenyl)-O-CH(H)-(4-chlorophenyl) | m.p., 71.5° C. |
| 15 | (3-chlorophenyl)-O-(2-chloro-5-phenoxyphenyl)-O-CH(H)-(4-chlorophenyl) | $n_D^{24.1}$ 1.6182 |
| 16 | (3-chlorophenyl)-O-(2-chloro-5-phenoxyphenyl)-O-CH(H)-(4-methylphenyl) | $n_D^{24.2}$: 1.6071 |
| 17 | (3,5-difluorophenyl)-O-(2-chloro-5-phenoxyphenyl)-O-CH(CH$_3$)-(4-chlorophenyl) | $n_D^{22.6}$: 1.5785 |

TABLE 2-continued

| Compound No. | Chemical structure | Physical constant |
|---|---|---|
| 18 | 3,5-difluorophenyl—O—(2-methyl phenyl with O—CH(H)—4-chlorophenyl substituent) | |
| 19 | 3-chlorophenyl—O—(2-bromo phenyl with O—CH(H)—4-chlorophenyl substituent) | |
| 20 | 3-chlorobenzyl—(2-chloro phenyl with O—CH(H)—4-ethylphenyl substituent) | |

In Formulation Examples as set forth below, parts and % are all be weight. The compound numbers correspond to those as shown in Table 2.

Formulation Example 1 (Emulsifiable Concentrate)

To a solution of 10 parts of each of Compounds Nos. 1 to 20 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

Formulation Example 2 (Wettable powder)

Twenty parts of each of Compounds Nos. 1 to 20 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

Formulation Example 3 (Granules)

Five parts of sodium dodecylbenzenesulfonate, 30 parts of bentonite and 60 parts of clay are added to 5 parts of each of Compound Nos. 1 to 3, 5 to 9, 11, 12 and 15 to 17, and the resultant mixture is pulverized and kneaded with a suitable amount of water. The mixture is granulated in a granulator and air-dried to give granules containing the active ingredient in 5%.

Formulation Example 4 (Granules)

Five parts of fine powders of synthetic hydrated silica, 5 parts of sodium dodecylbenzenesulfonate, 30 parts of bentonite and 55 parts of clay are added to 5 parts of each of Compound Nos. 4, 10, 13 and 14, and the resultant mixture is pulverized and kneaded with a suitable amount of water. The mixture is granulated in a granulator and air-dried to give granules containing the active ingredient in 5%.

Formulation Example 5 (Dusts)

To a mixture of 1 part of fine powders of synthetic hydrated silica, 1 part of an aggregating agent ("Driless B" manufactured by Sankyo Co., Ltd.) and 7.7 parts of clay, 0.3 part of each of Compound Nos. 1 to 3, 5 to 9, 11, 12 and 15 to 17 is added, and the resultant mixture is well pestled in a mortar and further stirred in a mixer. To the thus obtained mixture, there are added 90 parts of cut clay, followed by mixing to give dusts containing the active ingredient in 0.3%.

Formulation Example 6 (Dusts)

A mixture of 0.3 part of each of Compound Nos. 4, 10, 13 and 14 and 0.03 part of fine powders of synthetic hydrated silica is stirred well in a mixer and pulverized by the aid of a centrifugal pulverizer. To the resultant mixture, 0.97 part of fine powders of synthetic hydrated silica, 1 part of "Driless B" and 7.7 parts of clay are added, and the resulting mixture is pestled in a mortar and stirred in a mixer. Ninety parts of cut clay are added thereto, and further mixing is effected in a sack to give dusts containing the active ingredient in 0.3%.

Formulation Example 7 (Dusts)

A mixture of 0.3 part of each of Compound Nos. 1 to 3, 5 to 9, 11, 12 and 15 to 17, 2 parts of fenitrothion (0,0-dimethyl 0-(3-methyl-4-nitrophenyl)phosphorothioate as an organophosphorous insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 8 (Dusts)

A mixture of 0.3 part of each of Compound Nos. 4, 10, 13 and 14 and 0.03 part of fine powders of synthetic hydrated silica is stirred in a mixer and pulverized by a centrifugal pulverizer. After addition of 2 parts of fenitrothion (0,0-dimethyl 0-(3-methyl-4-nitrophenyl)phosphorothioate, 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

Formulation Example 9 (Dusts)

A mixture of 0.3 part of each of Compound Nos. 1 to 3, 5 to 9, 11, 12 and 15 to 17, 2 parts of BPMC (O-sec-butylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

Formulation Example 10 (Dusts)

A mixture of 0.3 part of each of Compound Nos. 4, 10, 13 and 14 and 0.03 part of fine powders of synthetic hydrated silica is stirred in a mixer and pulverized by a centrifugal pulverizer. After addition of 2 parts of BPMC (O-sec-butylphenyl N-methylcarbamate), 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

Formulation Example 11 (Dusts)

To a solution of 1 part of each of Compound Nos. 1 to 20 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1%.

Formulation Example 12 (Flowable concentrate)

To 40 parts of an aqueous solution containing 2 parts of polyvinyl alcohol, 10 parts of each of Compound Nos. 1 to 3, 5 to 9, 11, 12 and 15 to 17 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

Formulation Example 13 (Flowable concentrate)

To 28.5 parts of an aqueous solution containing 2 parts of polyvinyl alcohol, 20 parts of each of Compound Nos. 4, 10, 13 and 14 and 1.5 parts of sorbitan trioleate are added, and the resultant mixture is finely pulverized by the aid a sand grinder to give particles of less than 3 microns in average particle size. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 20%.

Formulation Example 14 (Oil soray)

Into a mixture of 5 parts of xylene and 5 parts of trichloroethane, 0.1 part of each of Compound Nos. 1 to 20 is dissolved, and the resultant solution is mixed with 89.9 parts of deodorized kerosene to give an oil spray containing the active ingredient in 0.1%.

Formulation Example 15 (Oil-bas-ed -aerosol)

A solution of 0.1 part of each of Compound Nos. 1 to 20, 0.2 part of tetramethrin (2,2-dimethyl-3-(2-methyl-1-propenyl)cyclopropanecarboxylic acid (1,2,3,4,5,7-hexahydro1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

Formulation Example 16 (Water-ba-sed aerosol)

A solution of 0.2 part of each of Compound Nos. 1 to 20, 0.2 part of d-allethrin ((2,2-dimethyl-3-(2-methyl1-propenyl)cyclopropanecarboxylic acid 2-methyl-4-oxo-3-(2-propenyl)-2-cyclopenten-2-yl ester), 0.2 part of d-phenothrin, 5 parts of xylene, 3.4 parts of deodorized kerosene and 1 part of an emulsifier ("ATMOS 300" ®, Atlas Chemical Co., Ltd.) in 50 parts of distilled water is filled in an aerosol container. After provision of a valve, 40 parts of a propellant (liquefied petroleum gas) is filled through the valve under reduced compression to give a water-based aerosol.

Formulation Example 17 (Fumigant)

Each of Compound Nos. 1 to 20 (100 mg) is dissolved in an appropriate amount of acetone, and the resultant solution is impregnated with a porous ceramic plate (4.0×4.0×1.2 cm) to give a fumigant.

The following Test Examples show some of test results which support the controlling effect of the aromatic compounds (I) on insect pests. The compound numbers correspond to those as shown in Table 2. The compounds used for comparison are as follows:

| Compound symbol | Chemical structure | Remarks |
|---|---|---|
| A | ⟨phenyl⟩–O–⟨phenyl⟩–OCH$_2$–⟨phenyl⟩–C$_2$H$_5$ | Compound disclosed in U.S. Pat. No. 3,987,102 |
| B | ⟨phenyl⟩–O–⟨phenyl(CH$_3$)⟩–OCH$_2$–⟨phenyl⟩–Cl | Compound disclosed in U.S. Pat. No. 3,987,102 |

Test Example 1

Metamorphosis inhibitory activity against brown rice planthopper nymphs:

An emulsifiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphs of brown rice planthopper (*Nilaparvata lugens*). After 10 days, the number of normal adults was counted to obtain an emergence inhibitory rate. The results are shown in Table 3.

TABLE 3

| Compound No. | Concentration (ppm) | Inhibitory rate (%) |
|---|---|---|
| 1 | 50 | 100 |
| 2 | 50 | 100 |
| 3 | 50 | 100 |
| 4 | 50 | 100 |
| 5 | 50 | 100 |
| 6 | 50 | 100 |
| 7 | 50 | 100 |
| 8 | 50 | 100 |
| 9 | 50 | 100 |
| 10 | 50 | 100 |
| 11 | 50 | 100 |
| 12 | 50 | 100 |
| 14 | 50 | 100 |
| 15 | 50 | 100 |
| 16 | 50 | 100 |
| 17 | 50 | 100 |
| A | 50 | 5 |
| B | 50 | 25 |
| No treatment | — | 5 |

The compound Nos. 6, 11, 15 and 16 also showed a 100% emergence inhibition at a concentration of 50 ppb.

What is claimed is:

1. An aromatic compound of the formula

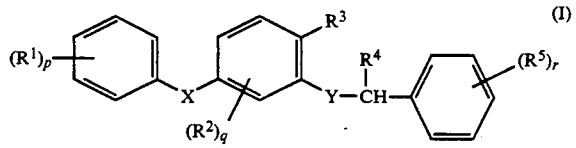

wherein $R^1$ is the same or different, and is a hydrogen atom, a fluorine atom or a chlorine atom; $R^2$ is a hydrogen atom; $R^3$ is a chlorine atom; $R^4$ is a hydrogen atom; $R^5$ is a chlorine atom or a methyl group; X is an oxygen atom or a methylene group; Y is an oxygen atom; p is an integer of 1 or 2; and q and r are each an integer of 1.

2. The compound according to claim 1, wherein $(R^1)_p$ is 3,5-F$_2$ or 3-Cl; $R^2$ is a hydrogen atom; $R^3$ is a chlorine atom; $R^4$ is a hydrogen atom; $R^5$ is a chlorine or a methyl group; X is an oxygen atom; Y is an oxygen atom; and q and r are each an integer of 1.

3. The compound according to claim 1, which is (2-chloro-1-(4-chlorobenzyloxy)-5-(3,5-difluorophenoxy))-benzene.

4. The compound according to claim 1, which is (2-chloro-5-(3,5-difluorophenoxy)-1-(4-methylbenzyloxy))-benzene.

5. The compound according to claim 1, which is (2-chloro-1-(4-chlorobenzyloxy)-5-(3-chlorophenoxy))-benzene.

6. The compound according to claim 1, which is (2-chloro-5-(3-chlorophenoxy)-1-(4-methylbenzyloxy))benzene.

7. A composition for controlling insect pests which comprises an effective amount of the aromatic compound according to claim 1 and an inert carrier.

8. A method for controlling insect pests which comprises applying an effective amount of the aromatic compound according to claim 1 to the insect pests or the locus where the insect pests propagate.

9. A composition for controlling insect pests which comprises an effective amount of the aromatic compound according to claim 2 and an inert carrier.

10. A method for controlling insect pests which comprises applying an effective amount of the aromatic compound according to claim 2 to the insect pests or the locus where the insect pests propagate.

11. The compound according to claim 1, which is a compound of the following formula:

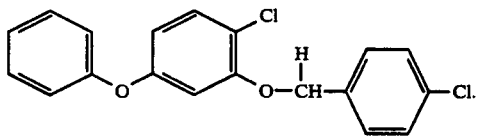

12. The compound according to claim 1, which is a compound of the following formula:

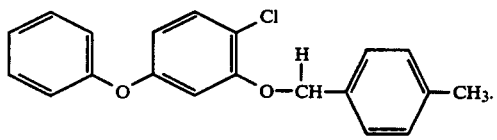

13. The compound according to claim 1, which is a compound of the following formula:

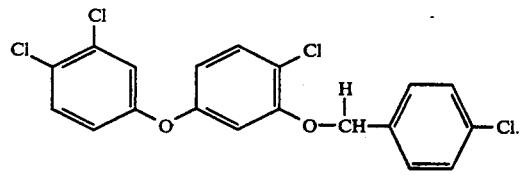

14. The compound according to claim 1, which is a compound of the following formula:

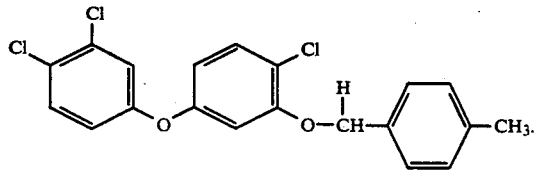

15. The compound according to claim 1, which is a compound of the following formula:

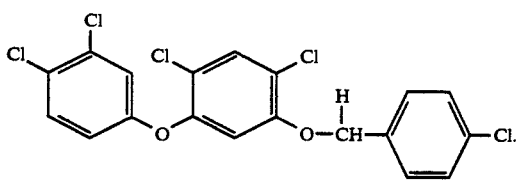
16. The compound according to claim 1, which is a compound of the following formula:
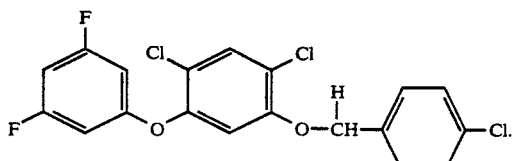
17. The compound according to claim 1, which is a compound of the following formula:
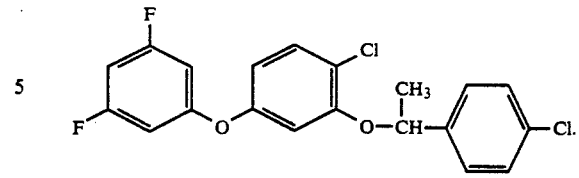
18. The compound according to claim 1, which is a compound of the following formula:
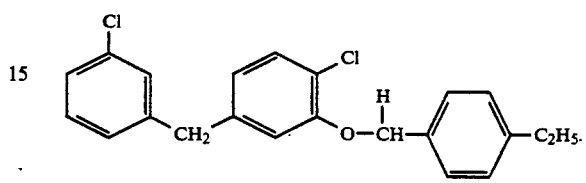
19. A compound of the following formula:
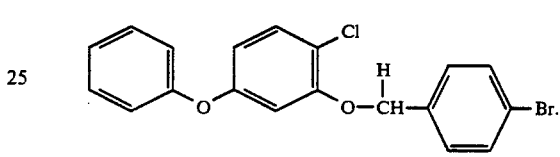
* * * * *